United States Patent [19]

Heinrich et al.

[11] 4,409,201
[45] Oct. 11, 1983

[54] PRESSURE-RESISTANT MICROCAPSULES WITH A POLYAMIDE SHELL AND A POLYURETHANE-POLYUREA INNER MASS AND PROCESS FOR THEIR MANUFACTURE

[75] Inventors: Rudolf Heinrich, Kelkheim; Heinz Frensch, Frankfurt am Main; Konrad Albrecht, Kelkheim, all of Fed. Rep. of Germany

[73] Assignee: Hoechst Aktiengesellschaft, Frankfurt am Main, Fed. Rep. of Germany

[21] Appl. No.: 268,386

[22] Filed: May 29, 1981

[30] Foreign Application Priority Data

May 31, 1980 [DE]  Fed. Rep. of Germany ....... 3020781

[51] Int. Cl.$^3$ .................. A61K 9/50; A61K 9/58; B01J 13/02
[52] U.S. Cl. .................................... 424/32; 8/526; 71/DIG. 1; 252/522 A; 264/4.1; 428/402.21; 521/128
[58] Field of Search .................... 252/316; 424/32, 22; 521/128

[56] References Cited

U.S. PATENT DOCUMENTS

| 3,429,827 | 2/1969 | Ruus ..................................... 252/316 |
| 3,577,515 | 5/1971 | Vandegaer ....................... 252/316 X |
| 3,639,306 | 2/1972 | Sternberg et al. .............. 252/316 X |
| 3,796,669 | 3/1974 | Kiritani et al. ........................ 252/316 |
| 3,812,056 | 5/1974 | De La Torriente et al. ...... 252/316 |
| 4,309,213 | 1/1982 | Graber et al. .................. 252/316 X |

FOREIGN PATENT DOCUMENTS

| 2757017 | 7/1979 | Fed. Rep. of Germany ...... 252/316 |
| 1257178 | 12/1971 | United Kingdom ................ 252/316 |

*Primary Examiner*—Richard D. Lovering
*Attorney, Agent, or Firm*—Curtis, Morris & Safford

[57] ABSTRACT

What are disclosed are pressure-resistant microcapsules comprising a polyamide shell having therein a structural mass of a polyurethane-polyurea polymer and an encapsulated water-immiscible liquid phase, and methods for making the same by dispersing a water-immiscible liquid phase in an aqueous phase and subsequently or simultaneously admixing therewith an aqueous solution of a diamine or polyamine, said dispersed phase comprising a polyamide forming acid compound, diisocyanate or polyisocyanate or a prepolymer thereof, and an inert organic aprotic hydrophilizing agent.

18 Claims, No Drawings

PRESSURE-RESISTANT MICROCAPSULES WITH A POLYAMIDE SHELL AND A POLYURETHANE-POLYUREA INNER MASS AND PROCESS FOR THEIR MANUFACTURE

The present invention relates to pressure-resistant microcapsules which have a shell composed of polyamide and contain, as the core material, a water-immiscible liquid phase and, if appropriate, active compounds, preferably pesticidally active compounds, in a polyurethane-polyurea-structured inner mass, and to a process for their preparation, and their use, in particular in plant protection.

The technique of microencapsulation has achieved increasing importance over the last few years, since this method enables substances of various states of aggregation to be enclosed in a non-reactive capsule. Numerous mechanical and chemical processes for manufacturing the capsules have already been described and used (in this context, compare, for example, I. E. Vandegaer, "Microencapsulation", Plenum-Press, New York-London; 1974). With regard to the use of microcapsules as carriers for various different substances, such as, for example, inks and dyestuffs, odor or flavor substances, pharmaceutical formulations, chemical reagents and the like, several attempts have also already been made to use plant protection agents in microcapsules.

Encapsulation of toxic plant protection agents, for example, is of particular importance from the point of view of safety in handling. A further advantage of encapsulating active compounds is that active compounds which are immiscible with one another or incompatible with one another can be combined. Encapsulation of active compounds can also be advantageous in reducing the odor nuisance in the case of odor-intensive active compounds. A further important advantage of encapsulation is that it is thereby possible to achieve release of the active compound in a controlled manner with respect to time and amount (depot action). As a result of this "slow release" effect, the active compound can remain active over a longer period of time and can thereby be better utilized, the number of applications necessary can be decreased and hence, finally, the total amount of active compound to be applied can be reduced. A reduction in the number of applications necessary means, as a result of the better utilization of the active compounds, less pollution of the environment by plant protection agent residues, in addition to a reduction in the expenditure on labor. Associated with the controlled release of active compound, better protection of the crop plants from phytotoxic damage also results.

One of the prerequisites for practical utilization of this technique is the necessary mechanical stability of the particles. For example, the abovementioned advantages can only be reckoned with in plant protection if the active compound carriers as far as possible remain undamaged during field application by machinery and also do not lose their specific use properties, in particular the ability to release the active compound slowly, when they are subjected to any mechanical load or are even damaged. Release of the active compound should take place only at the location of use, and in particular, for example, by diffusion processes or by slow destruction of the capsule wall. Diffusion of the contents of the capsule can be influenced, for example, by the thickness of the shell or of the capsule wall, by the solvents additionally included or, in particular, by the specific properties of the material forming the shell. The most diverse synthetic or naturally occurring high polymers have been used as the wall material, thus, for example, polyurethanes, polyureas, polyamides, polyesters, polyacrylates, polyolefins, cellulose derivatives, gelatin, polyvinyl alcohols and the like.

Each of these polymers has its own characteristic substance-specific values with regard to diffusion properties and chemical stability towards certain liquid or gaseous substances or substance mixtures.

Microcapsules with a polyamide shell are of particular interest for a number of active compounds, thus, for example, for certain highly volatile organic phosphorus compounds. Many processes for microencapsulating these or other active substances with polyamides are known and have been described in the literature. However, almost all the microcapsules which have polyamide shells and are manufactured by the processes already known have the disadvantage of insufficient mechanical stability for use in practice in the plant protection sector and in other areas of technology. A further disadvantage of the polyamide microcapsules is that the particles easily sediment and can be redispersed only with difficulty. Finally, almost all polyamide microcapsules also contain, in addition to the filling, undesirable residual amounts of the acid chlorides which are employed as starting components for capsule formation and which, for example, can react with the filling or can in other respects give rise to disorders or disadvantages.

It is already known that microcapsules with polyamide shells can be manufactured from diamines or polyamines and acid chlorides of difunctional or polyfunctional acids by polycondensation. The use of polyurea-polyamide copolymers for this process is also known.

Thus, for example, German Offenlegungsschrift No. 2,226,941 describes the manufacture of an insecticidal agent which contains microcapsules with methyl parathion or ethyl parathion as the core material in a casing or skin of crosslinked polyamide-polyurea, it being possible for the microcapsules to be in a mixture with an aqueous carrier or to be isolated by vacuum filtration. The manufacture of the microcapsules by encasing the water-insoluble core material dispersed in the form of droplets in the aqueous phase is effected by interfacial condensation of complementary intermediate compounds, which react to form crosslinked polyamide-polyurea polycondensates, the degree of crosslinking of the polycondensates being between 10 and 50%.

However, the polyamide-polyurea capsules manufactured in this manner have the disadvantage that, as a dispersion, they readily settle out from the carrier liquid when the dispersion is left to stand, it being possible for 2 or even 3 layers to be formed and also for the capsules readily to stick together. Moreover, the capsules, which have no inner structures, have the decisive disadvantages of only a low mechanical stability and inadequate compressive strength, which can have a very adverse effect and give rise to losses, for example when the microcapsules are used in plant protection during field application by machinery.

Microcapsules of polyurethane-polyurea with a polyurethane-polyurea-structured inner mass are known from German Offenlegungsschrift No. 2,757,017. They are manufactured by hydrolytic crosslinking of diisocyanate or polyisocyanate prepolymers, the latter being suspended, together with the core material, as the water-insoluble phase in an aqueous phase, and the core material containing an alkyl and/or alkoxyalkyl acetate as the solvent constituent. The microcapsules manufactured in this way do have a good compressive strength and also exhibit a good stability when subjected to mechanical load. However, a weakness lies, for example, in the known adverse diffusion properties of microcapsules with a polyurethane-polyurea shell, which properties prohibit encapsulation of numerous sensitive core materials in a polymer material of this type.

The present invention was thus based on the object of overcoming the known disadvantages of microcapsules which have polyamide shells but which, because of their advantageous distribution properties, are of interest for many applications, and of manufacturing pressure-resistant capsules which have a shell comprising polyamide and can be subjected to mechanical load.

It has now been found, surprisingly, that pressure-resistant microcapsules which have a polyamide shell and a polyurethane-polyurea-structured inner mass and contain, as the core material, a water-immiscible liquid phase and, if desired, active compounds, can be manufactured by a process which comprises dispersing a liquid, water-immiscible phase in an aqueous solution of a protective colloid. The water-immiscible phase contains, in an organic solvent, the difunctional or polyfunctional acid derivative required for polyamide formation, preferably an acid halide, and in particular an acid chloride, preferably of a difunctional or polyfunctional carboxylic acid, and a diisocyanate or polyisocyanate capable of polyurethane-polyurea formation by crosslinking with water, or a mixture thereof with organic compounds containing hydroxyl groups, preferably diols or polyols, or a diisocyanate prepolymer or polyisocyanate prepolymer, and the active compounds optionally to be encapsulated. If appropriate, the aqueous solution of a protective colloid may also contain surface active agents. An aqueous solution of a diamine or polyamine which is capable of polyamide formation and acid-binding agents is admixed with the dispersion, it also being possible for the aqueous solutions of the diamine or polyamine or of the acid-binding agent to be admixed with the aqueous protective colloid solution during the preparation of the dispersion. More in particular, the dispersed water-immiscible liquid phase contains an inert organic aprotic hydrophilizing agent which can dissolve water. The reaction of the components in the dispersion is preferably carried out at low temperatures.

The microcapsules formed after reaction of the components has taken place can be used in the resulting dispersion form or can be isolated by customary methods, for example, in particular, by spray-drying or by using dehydrating agents or by vacuum filtration, as a dry, free-flowing powder which can easily be redispersed in water.

The microcapsules according to the invention have high compressive strengths and are largely insensitive to damage by the mechanical loads occurring during customary processing and application operations. Surprisingly, they have a polyamide shell with the advantageous diffusion properties of polyamide and a structured inner mass, the structure of which is formed by a crosslinked polyurethane-polyurea polymer with a foam-cellular appearance, together with the core material. The fact that the capsule shells essentially comprise polyamide can be proved in a very simple and convincing manner by solubility tests with those solvents or solvent mixtures in which polyamides are soluble but, in contrast, crosslinked polyurethane-polyurea polymers are insoluble, such as, for example, concentrated formic acid.

On the basis of the manufacturing process, it was in no way to be expected that the polymeric capsule shells formed by the one-pot method according to the invention would have a material composition different from that of the simultaneously formed polymeric cellular structures of the inner mass, since, in a similar manner to the process described in German Offenlegungsschrift No. 2,226,941, the acid chloride and isocyanate component starting constituents reacted in an intimate mixture. Moreover, the core material of the microcapsules manufactured according to the invention also contains, for example, virtually no further residual amounts of unreacted acid chlorides, which is very advantageous.

The invention thus relates to new, pressure-resistant microcapsules which have a shell comprising polyamide and a polyurethane-polyurea-structured inner mass which contains a water-immiscible liquid phase and, if desired, active compounds, preferably pesticidal active compounds.

The invention furthermore relates to a process for the manufacture of pressure-resistant microcapsules with a shell comprising polyamide and a polyurethane-polyurea-structured inner mass containing a water-immiscible liquid phase and, if desired, active compounds, preferably pesticidal active compounds, in an aqueous dispersion by dispersing a liquid, water-immiscible phase which contains, in an organic solvent, the difunctional or polyfunctional acid derivative required for polyamide formation, preferably an acid halide, in particular the acid chloride, of a difunctional or polyfunctional carboxylic acid, as well as a diisocyanate or polyisocyanate or mixture thereof with organic compounds containing hydroxyl groups, preferably diols or polyols, or a diisocyanate or polyisocyanate prepolymer and the active compounds optionally to be encapsulated, in an aqueous solution of a protective colloid, which contains, if appropriate, surface-active agents, and simultaneously or subsequently admixing aqueous solutions of a diamine or polyamine and acid-binding agents, and reacting the components in the dispersion, wherein the dispersed and water-immiscible liquid phase contains an inert organic aprotic hydrophilizing agent which can dissolve water, and the reaction of the components in the dispersion is preferably carried out at low temperatures.

According to the invention, the proportion of inert organic aprotic hydrophilizing agent in the water-immiscible liquid phase can vary within a wide range. The range is preferably 1 to 85% by weight, in particular 4 to 50% by weight, relative to the water-immiscible liquid phase to be dispersed. Higher or lower proportions may also be expedient in some cases.

According to the invention, the capsule-formation reaction is preferably carried out at low temperatures, for example between 0° and 40° C., in particular between 0° and 20° C. It may be advantageous in each case to increase the temperature slightly, within this range, towards the end of the course of the reaction. In addition, however, higher reaction temperatures are not to be excluded. Since the rates of reaction in general increase sharply with increasing temperature, the quality of the capsules formed, and in particular of the capsule shells, can in some cases be impaired if the reaction proceeds too rapidly, especially if very reactive starting components are used, so that it is expedient and preferable to carry out the capsule-formation reaction according to the invention in a lower temperature range.

Possible inert organic aprotic hydrophilizing agents which can dissolve water are, for example, ketones, ethers or esters. Preferred hydrophilizing agents are, for example, aliphatic or cycloaliphatic ketones, ethers or esters, such as, for example, acetone, methyl ethyl ketone, diethyl ketone, cyclohexanone, methylcyclohexanone, isophorone, diethyl ether, diisopropyl ether, dioxane, tetrahydrofuran, ethyl acetate, methoxyethyl acetate, ethoxyethyl acetate, propyl acetate, butyl acetate and methoxybutyl acetate, or mixtures of these compounds, it being possible for the latter to be used either in anhydrous form or in a form which is partially or, in the case of compounds in which water has only a limited solubility, completely saturated with water. Ethyl acetate and 2-ethoxyethyl acetate are particularly preferred.

Further preferred inert organic aprotic hydrophilizing agents are alkyl acetates or alkoxyalkyl acetates of the formula I

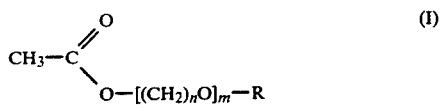

in which m denotes 0, 1 or 2, preferably 0 or 1, n denotes a number from 1 to 4, preferably 2, and R denotes $(C_1-C_5)$-alkyl.

Further possible organic aprotic hydrophilizing agents in the context of the invention are, in addition, aromatic, aromatic-aliphatic, aromatic-cycloaliphatic or hydroaromatic ketones, ethers or esters, as long as these compounds are capable of dissolving water and are miscible with the water-insoluble phase to be dispersed. The ketones, ethers or esters to be used according to the invention as hydrophilizing agents can also contain hetero-atoms.

According to the invention, the components for formation of the polyamide capsule wall material are chosen and matched with one another such that the capsule wall has an optimum elasticity and mechanical stability. Suitable difunctional or polyfunctional acid derivatives are, for example, the chlorides of succinic acid, glutaric acid, pimelic acid, azelaic acid, dodecanedicarboxylic acid, adipic acid or 1,3,5-benzenetricarboxylic acid, or compounds containing —SO$_2$Cl groups, such as 1,3-benzenedisulfonyl dichloride and 1,3,5-benzenetrisulfonyl trichloride.

Examples of suitable diamines or polyamines are ethylenediamine, hexamethylenediamine, diethylenetriamine, tetraethylenepentamine, pentaethylenehexamine, piperazine, phenylenediamine, toluylenediamine, 2,4,6-triaminotoluene trihydrochloride and 1,3,6-triaminonaphthalene.

Examples of isocyanate components are the aliphatic, aromatic, cycloaliphatic or araliphatic diisocyanates or polyisocyanates which are in themselves known, in particular toluylene 2,4- and 2,6-diisocyanate, hexahydrotoluylene 2,4- and 2,6-diisocyanate, diphenylmethane 4,4'-diisocyanate and higher homologs, polymethylenepolyphenylisocyanates (for example "PAPI" from Messrs. Upjohn Company), tetramethylene 1,4-diisocyanate and hexamethylene 1,6-diisocyanate. Possible diols or polyols are the aliphatic diols or polyols which are in themselves known, reaction products thereof with alkylene oxides, such as ethylene oxide or propylene oxide, polyhydric alcohols and polyalkylene glycols, in particular, for example, ethylene glycol, butylene glycol, 1,6-hexanediol, trimethylolpropane, glycerol, hexanetriol, polyethylene glycols and polypropylene glycols.

Particularly good results are obtained, for example, with an isocyanate prepolymer mixture which is obtained by reacting 2 to 3 moles of 1,2,6-hexanetriol or 1,1,1-trimethylolpropane, 1 mole of 1,3-butanediol and 1 mole of polypropylene glycol 1000 with 8 moles of toluylenediisocyanate, significantly less than the stoichiometric amount of the polyols employed being present. A particularly suitable solvent for the isocyanate prepolymer is a mixture of ethylene glycol acetate and xylene in a weight ratio of 5:1 to 1:5.

In general, diisocyanates or polyisocyanates which are appropriately slow to react, or isocyanate prepolymers which are relatively slow to react, are preferably used to avoid losses of the active compounds optionally to be encapsulated which may result from any possible reactions thereof with the isocyanate constituents required for capsule formation. Suitable isocyanate prepolymers of this type are, for example, reaction products of aliphatic, aromatic, cycloaliphatic or araliphatic diisocyanates or polyisocyanates and compounds which contain several OH groups, in particular, for example, diols or polyols, the diisocyanates or polyisocyanates being employed in excess, so that the reaction products formed still contain a sufficient number of free isocyanate groups and can react as polyisocyanates, the mean molecular weight of these reaction products preferably being about 300 to 10,000 [compare, for example, R. Vieweg and A. Höchtlen, Kunststoffhandbuch (Plastics Handbook) Volume VII, page 84 et seq., Carl Hanser Verlag, Munich, 1966].

The water-immiscible liquid phase to be employed in the process according to the invention generally contains the isocyanate component or isocyanate/diol or polyol component or isocyanate/prepolymer component in total amounts of 0.5 to 40% by weight, preferably 5 to 10% by weight, relative to the water-immiscible liquid phase. However, this amount, especially the maximum amount, is not limited to the values given, and can even be up to 70% by weight. On the other hand, if the amounts of the isocyanate components mentioned are too low, the desired mechanical stability of the microcapsules formed is in some cases no longer completely achieved.

The water-immiscible liquid phase also contains the acid derivative required for polyamide formation, preferably an acid halide, in an amount such that, in the microcapsules formed, the weight ratio of the polyamide forming the capsule shells to the polyurethane-polyurea polymer forming the inner structure, which ratio is in principle not critical and can be varied within a wide range, is preferably about 10:1 to 1:10.

Furthermore, the total proportion of the polymer material forming the capsule shells and the inner structures in the microcapsules manufactured according to the invention is preferably 5 to 50% by weight, in particular 12 to 30% by weight, relative to the total weight of the microcapsules, but the maximum amount is not limited to this range. Amounts below this range are in principle also possible, but they can lead to inadequate stability of the capsules.

The remainder to make up to 100% by weight of the water-immiscible liquid phase to be dispersed comprises, if appropriate, further water-immiscible organic solvents which are chemically inert towards isocyanates, water and the active compound optionally to be encapsulated. Possible solvents of this type are, for example, aromatic or aliphatic hydrocarbons, and also vegetable or synthetic oils or other esters, ethers or ketones which have not already been mentioned, in particular, for example, toluene, xylenes, methylnaphthalenes, dimethylnaphthalenes, paraffin oils, cyclohexane, 4-methyl-cyclohexane, benzylbenzoate, diphenyl ether, linseed oil, cottonseed oil or silicone oil.

The active compound optionally to be encapsulated can, for example, be liquid, or dispersed, at a temperature above its melting point, in the liquid water-miscible phase, if it is not itself soluble in the solvent components of the water-immiscible liquid phase and can be added to this phase in an appropriate solution. The liquid water-immiscible phase to be dispersed can contain the active compound, which is preferably a pesticidally active compound, but can also be, for example, a pharmaceutical or disinfectant, an odor substance, perfume substance or dyestuff or another chemical which does not react with an isocyanate, acid halide, diol or polyol or with water, in amounts of 0.1 to 80% by weight, preferably 1 to 60% by weight and in particular 5 to 40% by weight.

The aqueous phase in general contains about 0.5 to 10% by weight of a protective colloid, which can preferably comprise, for example, cellulose derivatives which are water-soluble or water-dispersible, such as, for example, carboxymethylcellulose or carboxymethylhydroxyethylcellulose, or polyvinyl alcohol or gum arabic. It is furthermore also possible to add non-ionic, anionic or cationic surface-active substances in amounts of 0.1 to 5% by weight. The amount of substances mentioned here which is added depends on the nature and composition of the water-immiscible liquid phase to be dispersed, the specific gravity of the active compound to be encapsulated, the desired size of the microcapsules, the reaction temperature and time, the stirring time and speed and the homogenizing intensity during the dispersing operation, and can easily be determined for an individual case by preliminary experiments.

Basic compounds, preferably alkali metal carbonates, alkali metal hydroxides or alkaline earth metal hydroxides, are employed in a known manner as acid-binding agents for neutralizing, for example, the hydrogen chloride as it is produced in stoichiometric amounts during the polyamide formation by reaction of the acid chlorides with the amines. The acid-binding agents are admixed with the aqueous dispersion as aqueous solutions, preferably mixed with aqueous solutions of the diamines or polyamines or, if appropriate, separately from but simultaneously with the latter, or they are even added to the aqueous protective colloid solution during the preparation of the aqueous dispersion, or are admixed with the aqueous protective colloid solution simultaneously with the water-insoluble phase during the dispersing operation, preferably with cooling to temperatures between about 0° and 20° C.

The proportion of diamines or polyamines in the aqueous phase is about 0.1 to 20% by weight, preferably 3 to 10% by weight, relative to the aqueous phase of the total reaction volume.

In carrying out the process according to the invention in practice for encapsulating any desired core material, a solution of the isocyanate prepolymer mixture, for example, is preliminarily mixed with the active compound optionally to be encapsulated, the difunctional or polyfunctional acid halide, the inert organic aprotic hydrophilizing agent, which can be partly or, if appropriate, completely saturated with water, and the additional organic solvents required, and this mixture is admixed with the aqueous phase, while stirring, this admixing advantageously being carried out in a zone of high turbulence. One of the generally customary industrial devices can be used to obtain a zone of high turbulence. These devices include, for example, stirred kettles with intensive stirrers, and also tubular reactors with the stirring devices suitable for such apparatus. The addition can be effected discontinuously or, if appropriate units are used, also continuously. Downstream homogenization devices may also be advantageous. A dispersion of the water-immiscible liquid phase in the aqueous phase in which the resulting droplets are present in the desired, selectable size, depending on the intensity of stirring or dispersing, is produced by this procedure. This size range is as a rule a particle diameter from 1 to 100 $\mu$m, preferably from 5 to 20 $\mu$m. However, for particular purposes it is also possible to produce particles with a larger diameter of, for example, 1 to 10 mm. It is necessary in this case only to choose the industrial devices appropriately for the preparation of the dispersion.

The liquid water-immiscible phase to be dispersed can comprise about 20 to 70% by volume of the total reaction volume of the dispersion, an amount of 30 to 60% by volume being preferred.

In some cases, it may be advantageous to add the aqueous solution of the amine and of the acid-binding agent dropwise to the continuous aqueous phase of the dispersion, while cooling and stirring intensively.

The temperature of the encapsulation system can be kept constant throughout the entire process, but it can also be changed after certain intervals of time, and should preferably be in the range from 0° to 40° C., preferably from 0° to 20° C. It may be advantageous to increase the temperature slightly within this range towards the end of the course of the reaction.

The reaction time is in general some minutes to several hours, in particular 2 to 5 hours, and in some cases it can be even longer before the inner structures are formed completely, for example up to 15 hours. In the course of the reaction, the polyamide shell forms most rapidly and can generally already be detected after a few minutes, while somewhat longer reaction times, preferably 2 to 5 hours, are required for complete formation of the polyurethane-polyurea inner structures. In some cases, up to 15 hours may even be necessary, especially at very low temperatures.

Surprisingly, microcapsules which have polyamide shells, the material of which can be defined, and which generally have a spherical shape and a smooth outer surface, and which are filled inside with the core material and a structured polyurethane-polyurea mass formed by crosslinking reactions, result from the manufacturing process according to the invention. As a result of this structured inner mass as the core material, the elasticity of the micropcasules is improved to such an extent that the particles according to the invention have a high compressive strength which it has not hitherto been possible to achieve for polyamide capsules, and very advantageous technological and specific use properties.

The inner structures of the particles manufactured according to the invention can be varied within a wide range of dimensions, depending on the manufacturing conditions. As can be established, for example, by scanning electron microscopy or by microscopic observation, they can be present as gel- or jelly-like micelles in the size range close to that of molecular dispersions, or with a sponge-cellular to foam-cellular structure in the microscopic size range, and they can also be shaped into macroscopically visible pore structures. These structures have a decisive effect on the elasticity and mechanical stability of the capsules formed. Microcapsules with a sponge-cellular or foam-cellular structure in the microscopic size range are preferred as carriers for active compounds, above all for plant protection agents.

It is also of importance, for the use of the particles according to the invention, for example as active-compound carriers in the field of plant protection, that no constituent of the particles exhibits undesirable phytotoxic actions. The particles carrying the pesticidally active compound can also readily be formulated into plant protection preparations after drying, which can be effected by known methods, advantageously by spray-drying, for example, or by using dehydrating agents or by vacuum filtration. They can be applied to fields without difficulty. The structured inner mass of the particles favors, inter alia, a delay in the release of active compound which is desired here, and thus leads to an improved depot action of the encapsulated active compounds. Moreover, a few hours after their manufacture, the particles are already free from residual amounts of acid chloride, for example, and, depending on the manufacturing conditions, where relevant they are also free from excess acid, without the activity of the encapsulated active compound being impaired. The severe sedimentation in aqueous suspensions which is otherwise observed with polyamide capsules is largely eliminated as a result of the fine gas bubbles which are formed during crosslinking of the isocyanate components by reaction with water and which remain in the capsule, the specific gravity of the capsule being reduced.

The invention is illustrated in more detail by the following examples.

PREPARATION EXAMPLES

Comparison Example 1

Preparation of microcapsules with a polyamide shell and without a structured inner mass, according to German Offenlengungsschrift No. 2,226,941, Example 1.

To prepare the aqueous phase, 3 g of polyvinyl alcohol (®Mowiol 40-88)+ are dissolved in 597 g of water and the solution is cooled to 3° C.

+ ®Mowiol 40-88: polyvinyl alcohol as a hydrolysis product of polyvinyl acetate (degree of hydrolysis: 87.7±1.0%), viscosity (based on a 4% strength aqueous solution): 40±2 cP To prepare the water-insoluble liquid phase, 29 g of sebacyl chloride and 10.8 g of polymethylene-polyphenylisocyanate ("PAPI", Messrs. Upjohn Company) are dissolved in 200 g of toluene.

The water-insoluble liquid phase, which is also cooled, is allowed to run, while stirring vigorously, into the aqueous phase, which is in a 2 liter stirred flask. A suspension of finely divided oil droplets of water-insoluble phase in the aqueous phase is formed.

A solution of 14.6 g of ethylenediamine, 16.6 g of diethylenetriamine and 25.5 g of anhydrous sodium carbonate in 200 ml of water is then added to the suspension in the cold and the mixture is stirred with a simple blade stirrer for about a further 2 hours at a temperature rising up to room temperature, in order to keep the material in suspension. The microcapsules formed are isolated and investigated. They can be tested, for example, by compressing sample capsules between two glass microscope slides. The resulting microcapsules are extremely pressure-sensitive and brittle and completely release the contents of the capsules immediately when damaged. The capsules have no structured inner mass.

Comparison Example 2

Preparation of microcapsules with a polyamide shell and without a structured inner mass.

To prepare the aqueous phase, a total of 4 g of polyvinyl alcohol (2 g of Mowiol 4-88++ and 2 g of Mowiol 18-88+++) are dissolved in 96 g of water and the solution is cooled to 3° C.

++Mowiol 4-88=polyvinyl alcohol as a hydrolysis product of polyvinyl acetate (degree of hydrolysis: 87.7±1.0%), viscosity (based on a 4% strength aqueous solution): 4±0.5 cP
+++Mowiol 18-88=polyvinyl alcohol as a hydrolysis product of polyvinyl acetate (degree of hydrolysis: 87.7±1.0%). Viscosity (based on a 4% strength aqueous solution): 18±1.5 cP. solution is cooled to 3° C.

To prepare the water-insoluble liquid phase, 2.5 g of sebacyl chloride are dissolved in 40 g of toluene, and 5 g of 2-ethoxyethyl acetate, which is saturated with water, and 5 g of ethyl acetate are added to this solution in the cold. The water-insoluble liquid phase, which is likewise cooled, is now allowed to run, while stirring vigorously, into the aqueous phase, which is in a 500 ml reaction flask. A suspension of finely divided oil droplets of water-insoluble phase in the aqueous phase is thereby formed. The resulting droplet size greatly depends on the shearing forces of the stirrer, and is between about 1 $\mu$m and 50 $\mu$m. When the desired particle size is reached, only a slight stirring motion is still required in order to keep the dispersed constituents in suspension. 5 g of 10% strength aqueous hexamethylenediamine solution and 1.5 g of 20% strength aqueous sodium carbonate solution are then added to the suspension, while stirring but without further cooling.

It is expedient subsequently to stir the resulting dispersion for some time at a temperature rising to room temperature. The microcapsules formed can be isolated from the dispersant, for example by vacuum filtration or by spray-drying. They are pressure-sensitive, completely release the contents of the capsules immediately when damaged and have no structured inner mass.

EXAMPLE 1

Preparation of microcapsules with a polyamide shell and a polyurethane-polyurea-structured inner mass To prepare the aqueous phase, a total of 4 g of polyvinyl alcohol (2 g of Mowiol 4-88 and 2 g of Mowiol 18-88) are dissolved in 96 g of water and the solution is cooled to 3° C.

To prepare the water-insoluble liquid phase, 2.5 g of sebacyl chloride are dissolved in 40 g of toluene, and 5 g of 2-ethoxyethyl acetate, 5 g of ethyl acetate which is saturated with water, and 7 g of a 50% strength solution of a prepolymer mixture which has been obtained by reacting 8 moles of toluylenediisocyanate (2,4:2,6 isomer ratio=80:20) with 1,2,6-hexanetriol, 1,3-butanediol and polypropylene glycol 1000 in molar amounts of 3:1:1 are added to the solution. A mixture of 2-ethoxyethyl acetate and xylene in a weight ratio of 1:3 is used as the solvent for the prepolymer mixture. The water-insoluble liquid phase is dispersed in the aqueous phase in the cold, and 5 g of 10% strength aqueous hexamethylenediamine solution and 1.5 g of 20% strength aqueous sodium carbonate solution are then immediately added at about 3° C., while stirring. After stirring the mixture for about a further 3 hours at a temperature rising to room temperature, the microcapsules are isolated and investigated.

As the example shows, capsule formation starts immediately after mixing the components in the dispersion. However, the compressive strength of the microcapsules formed is initially still low, for example after a reaction time of 10 minutes, but increases significantly in the course of time and reaches the desired values after 3-5 hours. Increasing the temperature towards the end of the reaction accelerates the course of the capsule formation reaction. After an appropriate period of time, a clearly structured inner mass of polyurethane-polyurea has formed, which extends throughout the entire inner space of the capsule and imparts the desired compressive strength and mechanical stability to the capsule. As solubility experiments in concentrated formic acid show, the capsule shells of the resulting microcapsules largely comprise polyamide, which dissolves in concentrated formic acid, whilst the polyurethanepolyurea inner structures do not dissolve in concentrated formic acid.

EXAMPLE 2

Preparation of microcapsules with a polyamide shell and a less pronounced polyurethane-polyurea inner structure The procedure followed is analogous to that in Example 1, but with the difference that only 3 g of the 50% strength solution of the prepolymer mixture mentioned in Example 1 are added to the water-insoluble liquid phase. As scanning electron microscopy shows, the inner structures which are thus formed but are less pronounced likewise extend over the entire interior space of the capsule.

Compared with the capsules of Comparison Examples 1 and 2, the microcapsules which are produced in this Example have a considerably greater compressive strength and better mechanical stability. As solubility experiments in concentrated formic acid show, the capsule shells of the resulting microcapsules essentially comprise polyamide, which dissolves in concentrated formic acid, while the polyurethane-polyurea inner structures do not dissolve in concentrated formic acid.

EXAMPLE 3

Encapsulation of an insecticidal phosphorus ester

The aqueous phase is formed analogously to that in Example 1, by dissolving 4 g of polyvinyl alcohol (2 g of Mowiol 4-88 and 2 g of Mowiol 18-88) in 96 g of water.

The water-insoluble liquid phase comprises 2.5 g of sebacyl chloride, 20 g of toluene, 20 g of Heptenophos+, 5 g of ethyl acetate which is saturated with water, 5 g of 2-ethoxyethyl acetate and 5 g of the 50% strength solution of the prepolymer mixture mentioned in Example 1. The procedure followed is otherwise as for the preparation of capsules as in Example 1.
+Heptenophos=7-chloro-bicyclo[3.2.0]-hepta-2,6-dien-6-yl dimethyl phosphate After a reaction time in the cold of 4–5 hours, while stirring and at temperatures which rise to room temperature at the end of the reaction, the capsule suspension is constantly stirred for a further 10–12 hours at room temperature. The particles are then isolated by spray-drying.

48 g of a free-flowing powder which comprises pressure-resistant microcapsules and has a bulk density and tap density of 40 and 45.5 g, respectively, per 100 ml and which contains 40% by weight of encapsulated Heptenophos are obtained. As solubility experiments in concentrated formic acid show, the capsule shells of the resulting microcapsules essentially comprise polyamide, while their inner structure comprises insoluble polyurethane-polyurea polymer.

EXAMPLE 4

Encapsulation of an insecticidal phosphorus ester

The aqueous phase is formed analogously to that in Example 1, by dissolving 1.5 g of Mowiol 18-88 and 3 g of gum arabic in 95.5 g of water.

The water-insoluble liquid phase comprises 5 g of benzenetricarboxylic acid trichloride, 15 g of triazophos++, 5 g of toluene, 5 g of ethyl acetate, 5 g of 2-ethoxyethyl acetate which is saturated with water, and 8 g of the 50% strength solution of the prepolymer mixture mentioned in Example 1. The capsule preparation is otherwise carried out as described in Example 1, and the resulting microcapsule particles are isolated by spray-drying. The yield and the properties of the particles are analogous to those of the product in Example 3.
++Triazophos=O,O-diethyl 1-phenyl-1,2,4-triazol-3-yl thionophosphate

EXAMPLE 5

Encapsulation of an insect bait

The aqueous phase is formed analogously to that in Example 1, by dissolving 1 g of Mowiol 40-88 and 2 g of gum arabic in 97 g of water.

The water-insoluble liquid phase consists of 3 g of sebacyl chloride, 5 g of disparlure [(Z)-7,8-epoxy-2-methyl-octadecane], 10 g of toluene, 5 g of ethyl acetate, 5 g of 2-ethoxyethyl acetate and 5 g of the 50% strength solution of the prepolymer mixture mentioned in Example 1. The capsule preparation is otherwise carried out as described in Example 1, but with the variation that 3 g of 10% strength aqueous diethylenetriamine solution and 1.2 g of 10% strength aqueous sodium carbonate solution are added to the dispersion of the water-insoluble liquid phase in the aqueous phase. After spray-drying the resulting capsule suspension, 28 g of a powder which is readily free-flowing and comprises pressure-resistant microcapsules are obtained. The average particle diameter is about 10 $\mu$m.

As solubility experiments in concentrated formic acid show, the capsule shells of the resulting microcapsules essentially comprise polyamide, while their inner structure comprises insoluble polyurethane-polyurea polymer.

We claim:
1. A pressure-resistant microcapsule comprising a single shell consisting essentially of a polyamide, a structured mass of a polyurethane-polyurea polymer occupying the volume within said shell, and an encapsulated water-immiscible liquid phase.
2. A pressure-resistant microcapsule as in claim 1 wherein the ratio by weight of polyamide forming said single shell to said polyurethane-polyurea polymer contained therein is from 10:1 to 1:10, and wherein the total amount of polymer in said shell and structured mass is 5 to 50 percent by weight of the total weight of the microcapsule.

3. A pressure-resistant microcapsule as in claim 2 wherein said total amount of polymer is 12 to 30 percent by weight of the total weight of the microcapsule.

4. A microcapsule as in claim 1 wherein said encapsulated liquid phase comprises a pesticidally active compound.

5. A method for making pressure-resistant microcapsules as in claim 1, which method comprises dispersing a water-immiscible phase liquid phase in an aqueous solution of a protective colloid, and simultaneously or subsequently admixing therewith an aqueous solution of a diamine or polyamine and of an acid binding agent, said water-immiscible liquid phase comprising a difunctional or polyfunctional acid derivative capable of polyamide formation with said diamine or polyamine, an inert organic aprotic hydrophilizing agent capable of dissolving water, and a member selected from the group consisting of diisocyanates and polyisocyanates, mixtures thereof with a compound containing hydroxyl groups, and prepolymers of a diisocyanate or polyisocyanate.

6. A method as in claim 5 performed at a temperature from 0° C. to 40° C.

7. A method as in claim 5 wherein said water-immiscible liquid-phase comprises 1 to 85 percent by weight of said inert organic aprotic hydrophilizing agent.

8. A method as in claim 5 wherein said inert organic aprotic hydrophilizing agent is a member selected from the group consisting of ketones, ethers, esters, and mixtures thereof.

9. A method as in claim 5 wherein said water-immiscible liquid phase comprises 20 to 70 percent by volume of the resulting dispersion.

10. A method as in claim 5 wherein said aqueous solution comprises from 0.5 to 10 percent by weight thereof of said protective colloid.

11. A method as in claim 5 wherein said water-immiscible liquid phase additionally comprises an active compound.

12. A method as in claim 11 wherein said active compound is a pesticidally active compound.

13. A method as in claim 11 wherein said active compound comprises from 0.1 to 80 percent by weight of said water-immiscible liquid phase.

14. A method as in claim 5 wherein said dispersing is effected in a zone of high turbulence.

15. A method as in claim 5 wherein said water-immiscible liquid phase is dispersed in the form of droplets have a diameter from 1 to 100 microns.

16. A method as in claim 5 wherein the microcapsules formed by the method are isolated by spray drying the dispersion.

17. A method as in claim 5 wherein said polyfunctional acid derivative is an acid halide.

18. A method as in claim 17 wherein said acid halide is an acid chloride.

* * * * *